(12) United States Patent
Weese et al.

(10) Patent No.: US 7,738,626 B2
(45) Date of Patent: Jun. 15, 2010

(54) SYSTEM FOR THE DETERMINATION OF VESSEL GEOMETRY AND FLOW CHARACTERISTICS

(75) Inventors: Juergen Weese, Aachen (DE); Alexandra Groth, Aachen (DE); Joerg Bredno, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 276 days.

(21) Appl. No.: 11/815,113

(22) PCT Filed: Jan. 31, 2006

(86) PCT No.: PCT/IB2006/050333

§ 371 (c)(1),
(2), (4) Date: Jul. 31, 2007

(87) PCT Pub. No.: WO2006/082558

PCT Pub. Date: Aug. 10, 2006

(65) Prior Publication Data

US 2008/0192887 A1 Aug. 14, 2008

(30) Foreign Application Priority Data

Feb. 4, 2005 (EP) .................................. 05100798

(51) Int. Cl.
*A61B 6/02* (2006.01)
(52) U.S. Cl. ............................................ 378/41; 378/8
(58) Field of Classification Search .................. 378/4, 378/41, 98.12
See application file for complete search history.

(56) References Cited

U.S. PATENT DOCUMENTS

| | | | | |
|---|---|---|---|---|
| 4,536,790 A | * | 8/1985 | Kruger et al. | 378/98.2 |
| 5,555,886 A | * | 9/1996 | Weng et al. | 600/454 |
| 5,583,902 A | * | 12/1996 | Bae | 378/8 |
| 6,373,920 B1 | * | 4/2002 | Hsieh | 378/98.11 |

(Continued)

FOREIGN PATENT DOCUMENTS

WO 0195615 A1 12/2001

(Continued)

OTHER PUBLICATIONS

M. Grass et al; "3-D Reconstruction of High Contrast Objects Using C-Arm Image Intensifier Projection Data", Computerized Medical Imaging and Graphics, pp. 311-321, 1999.

(Continued)

*Primary Examiner*—Edward J Glick
*Assistant Examiner*—Alexander H Taningco

(57) ABSTRACT

The invention relates to a method and a system for the simultaneous reconstruction of the three-dimensional vessel geometry and the flow characteristics in a vessel system. According to one realization of the method, vessel segments (41) of a parametric models are fitted to differently oriented X-ray projections ($P_1, P_k, P_N$) of the vessel system that are generated during the passage of a bolus of contrast agent, wherein the fitting takes the imaged contrast agent dynamics and physiological a priori knowledge into account. In an alternative embodiment, the vessel geometry is reconstructed progressively along each vessel, wherein a new segment of a vessel is added based on the continuity of the vessel direction, vessel radius and reconstructed contrast agent dynamics.

28 Claims, 3 Drawing Sheets

U.S. PATENT DOCUMENTS

| | | | |
|---|---|---|---|
| 6,426,994 B1 * | 7/2002 | Van Vaals | 378/98.12 |
| 6,442,235 B2 * | 8/2002 | Koppe et al. | 378/62 |
| 6,512,807 B1 * | 1/2003 | Pohlman et al. | 378/4 |
| 6,650,928 B1 | 11/2003 | Gailly et al. | |
| 6,711,433 B1 | 3/2004 | Geiger et al. | |
| 6,795,524 B2 * | 9/2004 | Hayashi | 378/98.12 |
| 2002/0123680 A1 * | 9/2002 | Vaillant et al. | 600/407 |
| 2003/0040669 A1 | 2/2003 | Grass et al. | |
| 2003/0114750 A1 * | 6/2003 | Brock-Fisher et al. | 600/431 |
| 2003/0123606 A1 | 7/2003 | Mollus et al. | |
| 2004/0066958 A1 | 4/2004 | Chen et al. | |
| 2004/0111023 A1 * | 6/2004 | Edic et al. | 600/425 |
| 2007/0083105 A1 * | 4/2007 | Miyazaki et al. | 600/410 |

FOREIGN PATENT DOCUMENTS

| | | |
|---|---|---|
| WO | 2005004038 | 1/2005 |

OTHER PUBLICATIONS

C.J. Henri, T.M. Peters; "3-D Reconstruction of Vascular Trees", Theory and Methodology, Med. Phys. 23, 1996.

S. Young et al; "3-D Vessel Axis Extraction Using 2D Calibrated X-Ray Projections for Coronary Modeling", Medical Imaging 2003, Image Processing, Proceedings of SPIE vol. 5032.

H. Schmitt et al; "An X-Ray-Based Method for the Determination of the Contrast Agent Propagation in 3-D Vessel Structure", IEEE Transactions on Medical Imaging, vol. 21, No. 3, 2002.

D. H. Ballard; "Generalizing the Hough Transform to Detect Arbitrary Shapes", Pattern Recognition, vol. 13, No. 2, pp. 111-122, 1981.

A. F. Frangi et al; "Multiscale Vessel Enhancement Filtering", Medical Image Computing and Computer Assisted Inverventions (MICCAI), Proc. LNCS 1496, pp. 130-137, 1998.

S. Young et al; "Vessel Segmentation for Visualization of MRA With Blood Pool Contrast Agents", Medical Image Computing and Computer Assisted Interventions (MICCAI), Lecture Notes in Computer Science 2208, 2001.

J. H. Hipwell et al: "Intensity Based 2D-3D Registration Of Cerebral Angiograms", IEEE Trans. Med Imag., vol. 22 (11), 2003.

J. B. Antoine Maintz and M. A. Viergever: "A Survey Of Medical Image Registration", Medical Image Analysis, vol. 2, (1), 1998.

* cited by examiner

SYSTEM FOR THE DETERMINATION OF VESSEL GEOMETRY AND FLOW CHARACTERISTICS

FIELD OF THE INVENTION

The invention relates to a method and an investigation system for the determination of the vessel geometry and the flow characteristics in the vessel system of a body region.

BACKGROUND OF THE INVENTION

For vascular diseases (e.g. neurovascular, peripheral, or coronary), important diagnostic information is gained from the shape of the vascular system in observation and its flow dynamics. Such information can for example assess tumors, ischemic stenoses, and arterio-venous malformations. A system that allows the such diagnostics is known from the US 2003/0040669 A1, according to which the vessel geometry is reconstructed in three dimensions based on a first sequence of rotational projections. The flow characteristics are then determined from a second sequence of projections from a constant direction, and matched with the three-dimensional vessel model. Due to the necessary generation of two image sequences, the patient load with contrast agent and X-radiation is however rather high for this method. Furthermore, as the dynamic flow is observed in one fixed projection geometry, flow information is only available for a subset of vessels which run approximately parallel to the image plane without occlusion from other vessels, therefore not providing complete diagnostic information.

SUMMARY OF THE INVENTION

Based in this situation it was an object of the present invention to provide means for the determination of vessel geometry and flow characteristics with high accuracy and reduced strain for the patient.

According to its first aspect, the invention relates to an investigation system for the determination of the vessel geometry and the flow characteristics in the vessel system of a body region, for example the cerebral arteries of a patient. The investigation system comprises an X-ray device for the generation of differently oriented projections of the vessel system, which may for example contain a rotational X-ray device and/or a bi-plane X-ray device. The investigation system further comprises a data processing unit that is coupled to the aforementioned X-ray device for receiving image data from it. The data processing unit comprises the usual hardware components like central processing unit, memory (RAM, ROM, hard disk etc.), I/O interfaces and the like together with appropriate software. The data processing unit is adapted to reconstruct a combined three-dimensional model of the vessel geometry including flow characteristics in at least one of the branches based on a single temporal sequence of differently oriented X-ray projections of the vessel system generated with the X-ray device during the passage of an injected bolus of a contrast agent. An important feature of said reconstruction is that the vessel geometry shall at least partially be based on the contrast agent dynamics (i.e. the temporal course of contrast agent concentration at points in space) as it is imaged in the projections, wherein the contrast agent dynamics is caused by the flow of the bolus together with the blood. Exemplary realizations of such a reconstruction will be described in more detail in connection with preferred embodiments of the invention.

An investigation system of the aforementioned kind has the advantage that it allows a reconstruction of the three-dimensional vessel geometry and of the flow characteristics based on a single sequence of X-ray projections. The load of the patient with contrast agent and X-radiation is therefore reduced accordingly. Despite the reduced number of available measurements, the reconstruction achieves a high accuracy because it makes use of modeled knowledge on contrast agent dynamics, i.e. the specific increase and decrease of X-ray attenuation—observed as "time-intensity curves" (TICs) in the projection images—due to the flow of contrast agent in the blood stream. Temporal changes associated with the passage of a bolus of contrast agent are thus exploited to obtain information on the vessel geometry and flow characteristics. This often even allows the reconstruction of "difficult" vessel geometries for which conventional methods yield no or ambiguous results.

According to an optional embodiment of the investigation system, the data processing unit is adapted to extract at least one set of features from the sequence of X-ray projections, wherein said features are related to the vessel geometry and/or the contrast agent dynamics. Image features that are suited for the task of vessel and contrast agent extraction include, but are not limited to:

- The position, local orientation, and local diameter of dark, elongated structures in the acquired projections. An Eigenvalue analysis of the Hessian matrix extracted at different scales is the preferred embodiment to extract this information.
- The time-intensity curve (TIC) at specific positions in the reconstructed volume extracted from all acquired projections. Each of these TICs shows a characteristic course that will fit to a modeled transit of a contrast agent bolus if and only if a vessel segment is present at the respective position. The TIC itself or fitted parameters like the time of bolus arrival, length of bolus, or the dispersion of the bolus front can be extracted and used as features.

In a preferred realization of the invention the data processing unit comprises a parametric model of both the vessel geometry and the contrast agent dynamics, wherein said model is defined at least in a sub-region of the observed body volume. A model of the vascular system with flow dynamics is typically a tree data structure built from elements that represent tubular vessel segments. Such a model element may particularly be a cylinder with fixed diameter, length, position and orientation in the reconstructed volume. Additionally the volume of blood flow and a resulting TIC expected at this tubular segment are a part of the model for each element. A model TIC can e.g. be represented by the convolution of the injected contrast agent pattern with the modulation function that is obtained when the mix of blood and contrast agent flows through the tubular vessel segments up to the segment for which a TIC prediction is required.

In a further development of the aforementioned system, the data processing unit is adapted to reconstruct an instance (i.e. a variant of the model with particular parameter values) of the model that fits both to the acquired sequence of X-ray projections (or to features extracted therefrom) and to plausibility rules derived from physiological knowledge about vessel geometry and/or contrast agent dynamics. For such a fit, quantitative plausibility scores may be computed that describe the similarity of a model instance to features of acquired data and the plausibility of the model itself with respect to physiological a-priori knowledge. Various algorithms are known that match data models to observed features based on such scores, wherein these algorithms are also applicable to the model which specifically describes a vascular subsystem with blood flow and contrast agent dynamics. Two preferred embodiments of such algorithms will be described below.

The approaches described above are preferably combined to yield a model-based extraction of vascular geometry and contrast agent dynamics with the following three modules, each of which can be implemented on the data processing unit in one or more different ways:

1. A module with algorithms to extract one or more sets of features from the acquisition that are specifically selected to allow for the extraction of contrasted vessels.
2. A module with a geometric and flow-dynamic model of a vascular subsystem.
3. A module with an optimization algorithm that determines the instance of the aforementioned model that best fits to the observed features in the current acquisition.

In a first preferred embodiment of the reconstruction algorithm, the parametric model consists of elements corresponding to local (tubular) vessel segments together with local contrast agent dynamics, wherein each of said model elements is associated with a local score value. The data processing unit will then preferably be adapted to fit locally (i.e. in every point in space) the parameters of one tubular vessel segment and of an associated model of the contrast agent dynamics (or the observed TIC) in said vessel segment to the sequence of projections. For each point in space, the plausibility score for the model, the image features, and the TIC at this position are preferably combined to one final score which is inserted into a three-dimensional map. Then, a vessel section of interest can be reconstructed and displayed if the user gives its start and end point. A minimal cost path through the score map between these user-given points will for example extract the complete vessel section together with the contrast agent dynamics. Therefore, the geometry and blood flow of such a vessel of interest is presented to a user after only one acquisition and the selection of the start- and endpoint of a diagnostically relevant part of the vascular system. The front propagation algorithm is one known method to extract a minimal cost path between two points in a score map.

In a second preferred embodiment of the reconstruction algorithm, the data processing unit is adapted to reconstruct the flow characteristics and the vessel geometry in three dimensions progressively along the vessels with an iterative tracking algorithm. Starting at one (e.g. manually) selected point in the reconstructed volume, such an algorithm subsequently adds tubular segments to the already known model instance. The direction of each new segment is determined as the direction in which the highest plausibility score is obtained. This plausibility score may be computed as a weighted combination of different features, e.g.:

The consistency of a hypothetical direction of the new tubular segment in 3D is compared to all planar directions extracted as features from the projection images.

The TIC, i.e. the imaged contrast agent dynamics in the new segment is predicted from the TIC of the last already known segment and then compared to the TIC extracted at the new end point of the segment in the hypothetical direction.

In a preferred embodiment, the plausibility score for one individual projection is computed as reciprocal of the deviation between the 3D direction and the direction extracted in the projection at this point, multiplied with the difference between the observed TIC at this point in the projection and the TIC predicted from the model for the time at which this projection was acquired. For each hypothetical direction, the sum of plausibility scores over all projections is collected and finally, a tubular segment in the direction with the highest score is added to the model. In an iteration, segments are added until either the observed vessel segment leaves the observed volume or until no more sufficiently high plausibility scores can be extracted.

In both embodiments described above, an increase in robustness in comparison to algorithms that work on static vessel trees is obtained because the additional information on contrast agent dynamics can solve ambiguities that frustrate the application of conventional methods to acquisitions with a static, completely opaque vessel tree.

A parametric model (element) of contrast agent dynamics may particularly comprise a function describing a contrast peak with the phases of inflow, plateau, and outflow of contrast agent embedded in phases without any contrast agent. With a peak function of this kind the observed contrast appearances can be characterized by a small number of parameters but nevertheless with a high accuracy.

In an alternative embodiment, the data processing unit is adapted to predict a function ($c(t, \vec{p})$) that represents the amount of contrast agent at any point in the vascular model when contrast agent is injected upstream and transported by convection and diffusion of a fluid through tubular structures of a known geometry up to this point. This approach yields very realistic TICs as it takes the concrete vessel geometry through which a bolus has flown between injection and observation into account.

The investigation system preferably comprises an input device like a keyboard or a mouse by which a user can enter information. This information may particularly comprise the position of one or more user-defined seed points which are taken as starting points for a progressive three-dimensional reconstruction of the vessel geometry.

The investigation system typically comprises a display unit like a monitor for displaying the reconstructed vessel geometry and/or the reconstructed flow characteristics. Thus the results of the reconstruction process can be presented in a user-friendly intuitive way.

The invention further comprises a method for the determination of the vessel geometry and the flow characteristics in the vessel system of a body region, comprising the following steps:

a) The injection of a bolus of contrast agent into the vessel system. Such an injection may for example be accomplished with the help of an automatic injection device.
b) The generation of a temporal sequence of X-ray projections of the vessel system during the passage of the aforementioned bolus from different directions.
c) The reconstruction of a three-dimensional model of the vessel geometry and of a model of the flow characteristics in said vessel geometry at least partially based on the imaged contrast agent dynamics caused by the bolus.

Finally, the invention comprises a record carrier, for example a floppy disk, a hard disk, or a compact disc (CD), on which a computer program for the determination of the vessel geometry and the flow characteristics in the vessel system of a body region is stored, wherein said program is adapted to execute a method of the aforementioned kind.

The method and the record carrier have similar features like an investigation system as it was described above. For more information on details, advantages and further developments of them reference is therefore made to the description of said investigation system.

These and other aspects of the invention will be apparent from and elucidated with reference to the embodiment(s) described hereinafter.

BRIEF DESCRIPTION OF THE DRAWINGS

In the following the invention is described by way of example with the help of the accompanying drawings in which.

DESCRIPTION OF PREFERRED EMBODIMENTS

Figure 1:
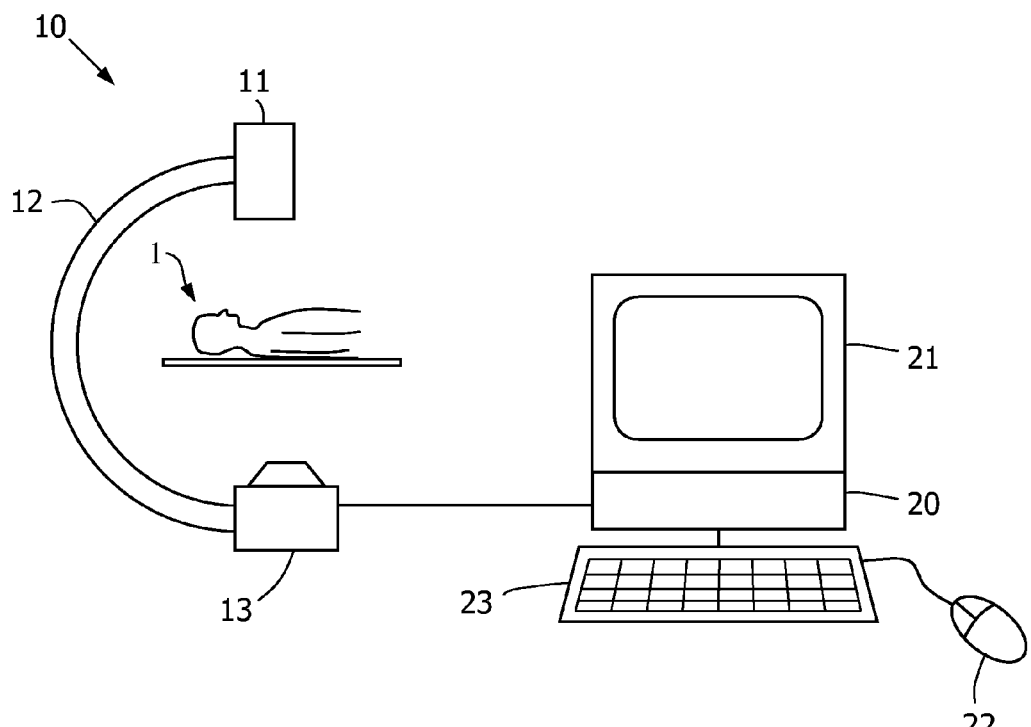
FIG. 1 shows schematically an investigation system according to the present invention.

FIG. 1 shows schematically an investigation system as it may be used in connection with the present invention. The system comprises a rotational X-ray device 10 with an X-ray source 13 facing an X-ray detector 11, wherein both components are coupled via a C-arm 12. A patient 1 is positioned in the centre of the X-ray device 10 such that X-ray projections of the vessel system in a body region of said patient 1 can be generated from different directions. Furthermore, the X-ray device 10 is coupled to a data processing unit 20, for example a workstation, which is adapted to control the X-ray device 10 and particularly to process image data received therefrom. The data processing unit 20 is also connected to a monitor 21 on which a reconstructed vessel tree and its flow characteristics can be displayed, wherein the flow may for example be represented by a film sequence or in a color code of flow velocities. Via a keyboard 23 and a mouse 22 connected to the workstation 20 a user can interactively enter information.

Figure 2:
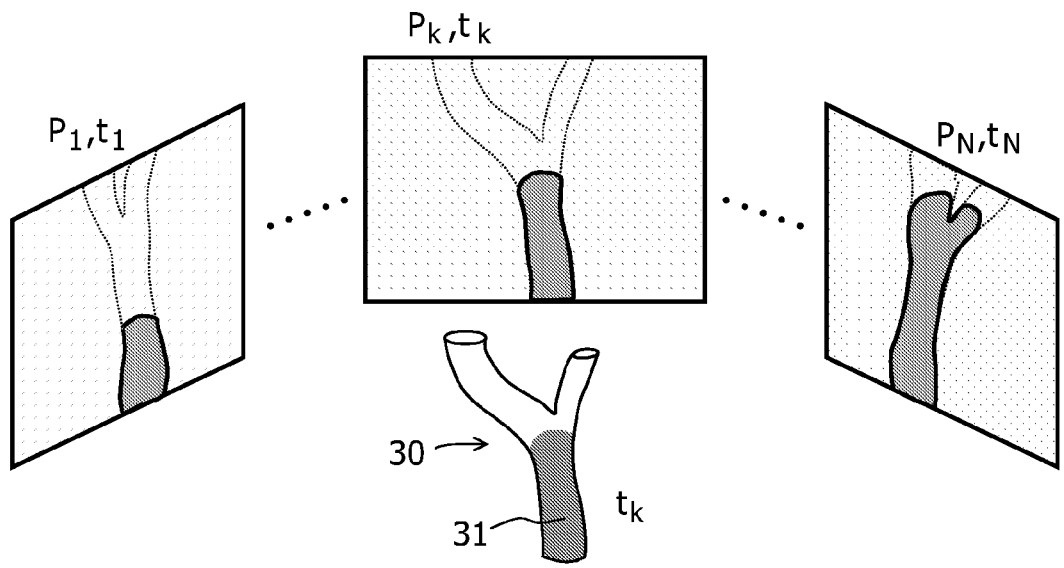
FIG. 2 shows schematically a section of a vessel and three projection images thereof taken at different times and from different directions.

FIG. 2 illustrates the geometrical relations between a section of a vessel 30 (depicted at time $t_k$) and a sequence of projections $P_1, \ldots P_k, \ldots P_N$ of it taken consecutively from different directions by the X-ray device 10 of FIG. 1 at respective times $t_1 < \ldots t_k < \ldots t_N$. The sequence of projections $P_1, \ldots P_N$ is generated while a bolus 31 of a contrast agent (typically injected via a catheter) passes through the vessel system. In currently common imaging devices, a typical number N of projections is about 100. As the projections $P_1, \ldots P_N$ are generated at different times, they show the bolus 31 at different positions with respect to the vessel 30. Vessel sections filled with no contrast agent are indicated with dotted lines in the projections $P_1, \ldots P_N$, though they are typically not visible one real X-ray projections.

Figure 3:
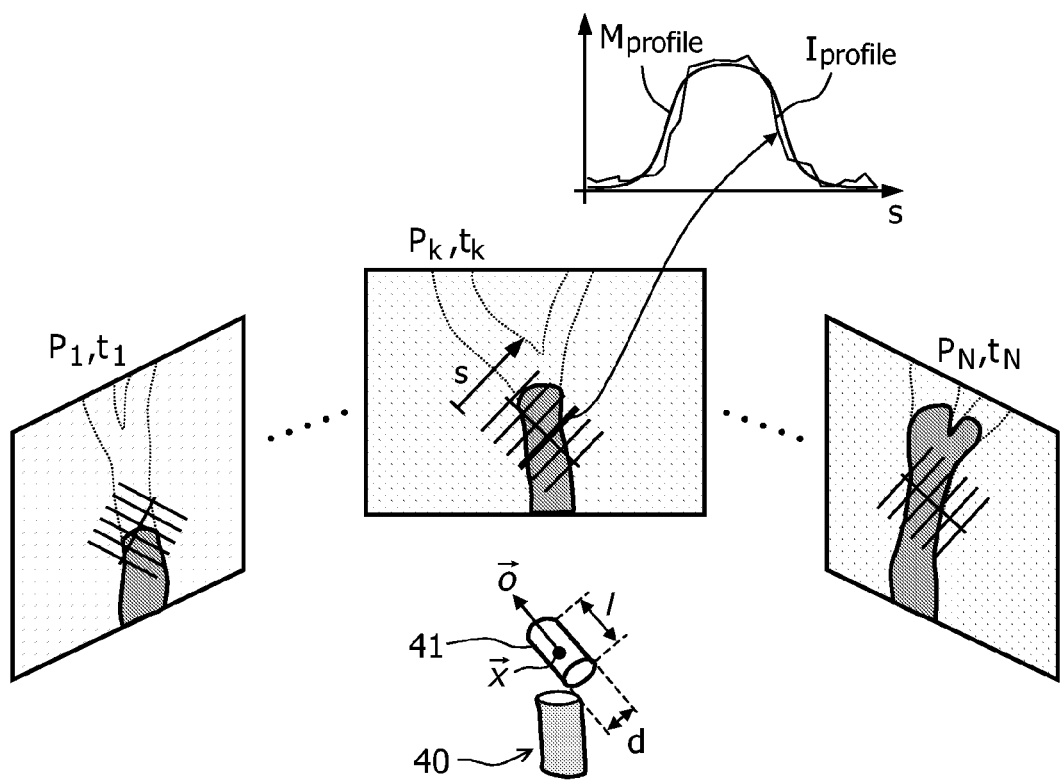
FIG. 3 illustrates the computation of a plausibility score for one point in space according to the first preferred embodiment where a cylindrical segment and a TIC extracted at this position are assessed.

FIG. 3 illustrates the creation of a plausibility score map for a first method for the combined three-dimensional reconstruction of vessel geometry and flow characteristics based on the arrangement of FIG. 2.

Dedicated acquisition protocols are used in or developed for catheter laboratories including bi-plane imaging or rotational acquisition to access the 3D vessel geometry (see e.g. C. J. Henri, T. M. Peters: "Three-dimensional reconstruction of vascular trees. Theory and methodology", Med. Phys. 23(2):197, 1996; M. Grass, R. Koppe, E. Klotz, R. Proksa, M. H. Kuhn, H. Aerts, J. Op de Beek, R. Kemkers: "3D reconstruction of high contrast objects using C-arm image intensifier projection data", Computerized Medical Imaging and Graphics, 23(6):311, 1999; S. Young, B. Movassaghi, J. Weese, W. Niessen, V. Rasche: "3D vessel axis extraction using 2D calibrated X-ray projections for coronary modeling in Medical Imaging 2003: Image Processing", M. Sonka, J. M. Fitzpatrick, eds.; Proceedings of SPIE Vol. 5032, 2003). In addition, there are approaches that map properties extracted from the contrast agent flow (e.g. flow front, velocities) onto previously reconstructed vessel geometries (see e.g. H. Schmitt, M. Grass, V. Rasche, O. Schramm, S. Hähnel, K. Sartor: "An X-ray based method for the determination of the contrast agent propagation in 3-D vessel structures", IEEE Transactions on Medical Imaging, 23(3):251, 2002).

The basic idea of the present invention is a dedicated, model-based reconstruction that uses model knowledge on the geometry of a vessel and its dynamic appearance when contrast agent flows through, to extract both, the 3D geometry and its visual appearance due to contrast flow in a single step.

The starting point for a simultaneous reconstruction of vessel geometry and contrast agent dynamics (wherein the "contrast agent dynamic" is defined as the temporal course of contrast agent concentration at a particular point in space and in the model of the vascular tree) is the set of projection images $P_1, \ldots P_N$ together with the time stamps $t_1, \ldots t_N$ acquired during and directly after contrast injection with the geometry parameters $\vec{g}_1, \ldots \vec{g}_N$. One example is a set of two image time series showing perpendicular projections with fixed projection direction as they can be obtained from a bi-plane system. Another example (shown in FIGS. 2-4) is a rotational acquisition over 180° or more showing contrast in- and outflow at the start and the end of the sequence. Depending on the acquisition protocol and the availability of suitable images, images without contrast agent can be subtracted from respective images prior to reconstruction.

In the first exemplary realization of a reconstruction algorithm illustrated in FIG. 3, the TIC for each voxel as estimated from the sequence of projections, and the original grey-values in the X-ray projections are used as features.

Figure 6:
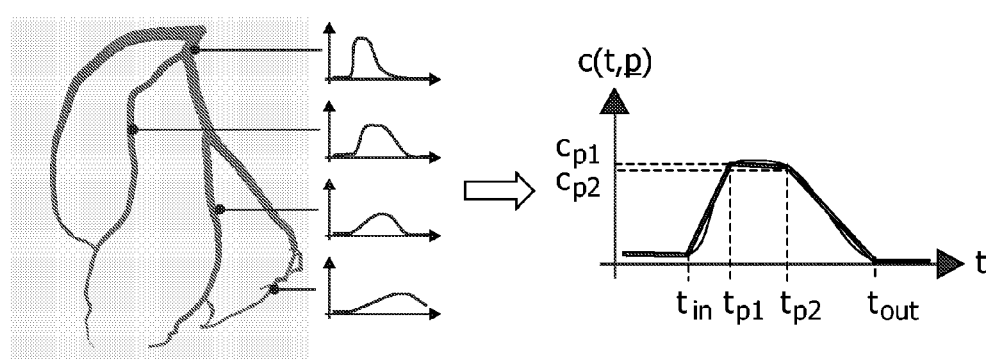
FIG. 6 shows an exemplary model function for the contrast agent dynamics or its imaging as TIC, respectively.

The parametric model consists of a set of cylindrical elements 41 for the geometry and a model of valid TICs, wherein each cylindrical element 41 is defined by its length l, an adjustable orientation $\vec{o}$, and an adjustable diameter d (cf. FIG. 3);

the predicted result of the X-ray projection of such a cylinder 41 is modeled by profiles $M_{profile}$ of grey-levels that appear over the cylinder's cross section; and the TIC and/or the contrast agent dynamics in such a cylinder is given by a model with a few parameters $\vec{p}$. (Remark: in the following the contrast agent dynamics and its image, the TIC, are often treated like synonyms because they basically relate to the same phenomenon). This model can, for instance, be composed of five line segments (no contrast, contrast inflow, plateau, contrast outflow, no contrast) as shown in FIG. 6.

Two different optimization algorithms are used in this embodiment: A first part determines the best orientation, size, and modeled TIC of one cylinder element 41 for all voxels in the reconstructed volume. The residual mismatch between the extracted features and the best modeled vessel segment is exported as plausibility score for this voxel. A second optimization algorithm then finds an optimal path through the volume between the start and the end point of a vessel segment of interest. In consequence, the second optimization algorithm has to find a path with a minimal total sum of local mismatches. The front propagation algorithm which simulates the propagation of a wave according to a local speed function (which is defined by said plausibility score in this application) is a preferred embodiment for this optimal path extraction. Usually the speed function is defined by applying a geometric filter on the projections or by matching a geometric model such as a cylinder (cf. S. Young et al., above). Within the approach suggested here, the cylinder model element of FIG. 3 that includes the expected and observed TIC is used for the definition of the speed function in the way that will be described in the following.

For each point $\vec{x}$ in space, a projection of the aforementioned cylinder 41 according to a distinct projection geometry leads to a set of grey-value profiles $M_{profile}$ along a direction s perpendicular to the axis of the projected cylinder model 41 of the vessel segment. The centre of these profiles should coincide with the centerline of the cylinder 41 and the length of the profiles should be about two to three times larger than the projected vessel diameter d. The profiles $M_{profile}$ are compared with the spatially corresponding grey-value profiles $I_{profile}$ in the acquired projections $P_1, \ldots P_k, \ldots P_N$ using a proper similarity measure S as they are also known from image registration (cf. J. B. A. Maintz, M. A. Viergever: "A survey of medical image registration", Medical Image Analysis, 2(1), 1998; J. H. Hipwell, G. P. Penney, et al.: "Intensity based 2D-3D registration of cerebral angiograms", IEEE Trans. Med. Imag. 22(11): 1417, 2003).

In the case of a vascular structure on a homogeneous background the similarity measure can, for instance, be defined by $$S(I_{profile}(\vec{o}), M_{profile}(\vec{o}, d, \vec{p})) = \sum_{\substack{pixels\ i \\ in\ profile}} (I_{profile}(\vec{y}_i; \vec{o}) - \bar{I}_{profile}(\vec{o}) - (M_{profile}(\vec{y}_i; \vec{o}, d, \vec{p}) - \bar{M}_{profile}(\vec{o}, d, \vec{p})))^2$$

where $I_{profile}(\vec{y}; \vec{o})$ and $M_{profile}(\vec{y}; \vec{o}, d, \vec{p})$ denote the grey-value profile in the projection image and of the projected cylinder model with $\vec{y}_i$ being the position vector of the considered pixel i (the dependence of the similarity measure S on the currently considered position $\vec{x}$ in space is not particularly denoted in the formula). The image profile $I_{profile}(\vec{y}; \vec{o})$ is geometrically defined by the projection geometry and the cylinder orientation. The profile $M_{profile}(\vec{y}; \vec{o}, d, \vec{p})$ of the projected model depends in addition on the cylinder diameter d and the parameters $\vec{p}$ characterizing the contrast agent dynamics. It should be noted in this context that $M_{profile}$ is considered at the point in time that corresponds to the projection from which $I_{profile}$ is taken (i.e. $M_{profile}$ is considered at $t_k$ if $I_{profile}$ stems from $P_k$). $\bar{I}_{profile}(\vec{o})$ and $\bar{M}_{profile}(\vec{o}, d, \vec{p})$ denote the average grey-values of respective profiles. The first part of the optimization procedure determines the locally optimal model parameters $\vec{o}$, d, and $\vec{p}$ for each spatial position $\vec{x}$ by finding the minimum of an objective function V, which is obtained by summing up the similarity measures for all projections and profiles:

$$V(\vec{o}, d, \vec{p}) = \sum_{projections} \sum_{profiles} S(I_{profile}(\vec{o}), M_{profile}(\vec{o}, d, \vec{p})).$$

The residual value $V_{opt} = V(\vec{o}_{opt}, d_{opt}, \vec{p}_{opt})$ of the objective function V, e.g. the smallest V that could be determined, is used to define the plausibility score for the voxel at position $\vec{x}$. As mentioned above, the front propagation algorithm finds an optimal cost path via an analogy: Goodness measures are interpreted as local possible speed, then the fastest connection between two given points is determined. The front propagation algorithm therefore interprets the determined plausibility scores as local propagation speeds here. Consequently, a function is required that results in high values for low residual $V_{opt}$ and vice versa. Having determined the optimum model parameters $\vec{o}_{opt}, d_{opt}$, and $\vec{p}_{opt}$ at position $\vec{x}$, such a propagation speed F can be defined by $$\sum_{projections} \sum_{profiles} S(I_{profile}(\vec{o}_{opt}), 0_{profile}) - V(\vec{o}_{opt}, d_{opt}, \vec{p}_{opt}),$$

where $0_{profile}$ represents a constant zero profile, i.e. a profile with no vessel. In that way, above difference characterizes the change of the similarity measure due to the presence of a vessel segment. A strictly monotonous function can be applied to the above difference to provide the front propagation algorithm with data in an expected range with a suitable selection of propagation speeds for the varying plausibility scores.

When vessel geometry and contrast dynamics reconstruction is done by front propagation in 3D, an initial region of interest is defined via a set of user-defined seed points (one or more). The region surrounding each of these points is iteratively expanded according to the simulated propagation of a wave with the local speed response $F(\vec{x})$ (which was computed here by the first part of the optimization), and then the time of arrival of the front, $T(\vec{x})$, at newly included voxels is determined by solving the propagation equation $|\Delta T|F=1$.

After propagation, the 'shortest path' from any of the selected points back to the 'nearest' seed point can be traced by following the path of minimal time within the time field obtained during propagation. With a proper speed response and properly selected points at the start and the end of a vessel segment, the geometric properties (e.g. centerline and diameter) of this segment can be reconstructed in that way.

As the determination of $V_{opt}$ for each voxel can be very time consuming, the optimal parameters determined for one 3D point $\vec{x}$ can be stored and propagated to neighboring points as initial guess during the iterations of the front propagation algorithm. This means that the two optimization steps are combined, wherein the local optimization is only performed for voxels that possibly lie on the optimal path, and wherein the local optimization at a new voxel may be accelerated by using initial values of already known neighboring voxels (see also S. Young, V. Pekar, J. Weese: "Vessel segmentation for visualization of MRA with bloodpool contrast agent in Medical Inage Computing and Computer Assisted Interventions (MICCAI 2001)", W. J. Niessen, M. A. Viergever, eds.; Lecture Notes in Computer Science 2208, 2001). The optimal parameters for the reconstructed vessel segments can, finally, be retrieved during determination of the 'shortest path' by following the path of minimal time within the time field obtained during propagation.

Figure 4:
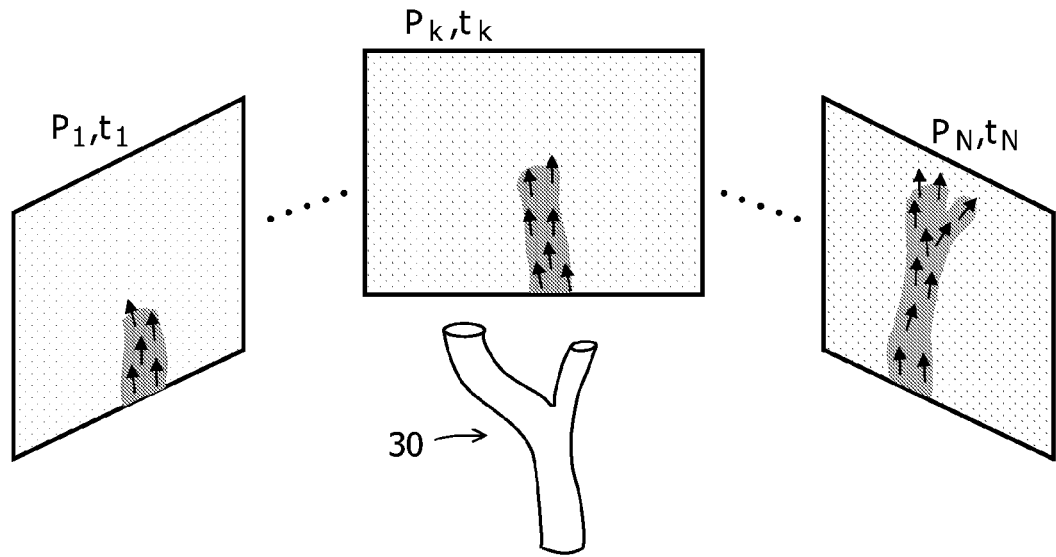
FIG. 4 illustrates the two-dimensional extraction of vessel direction and radius for the reconstruction of the 3D vessel geometry in the arrangement of FIG. 2 which is used as feature in a second preferred embodiment.
Figure 5:
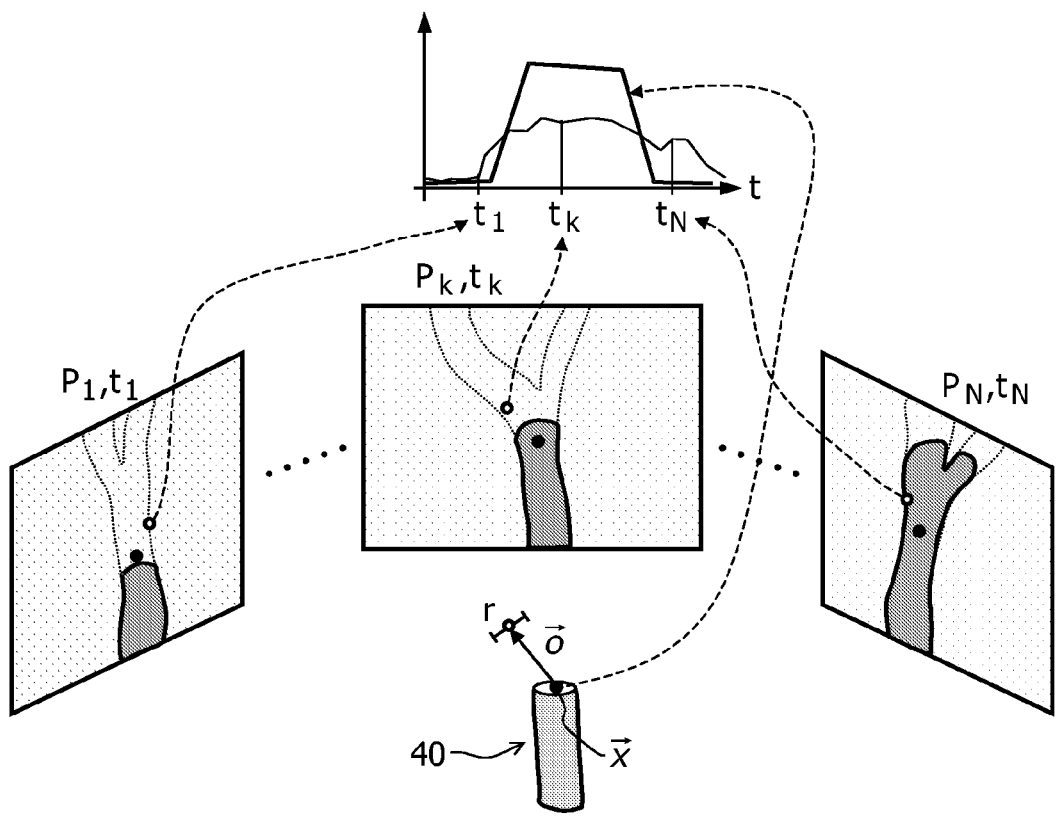
FIG. 5 illustrates one step of the progressive reconstruction of the vessel according to the second preferred embodiment based on a preprocessing according to FIG. 4.

FIGS. 4 and 5 illustrate a second method for the combined three-dimensional reconstruction of vessel geometry and flow characteristics. In this method, a-priori knowledge is provided by a dedicated 3D tracking algorithm that takes into account the coherence of contrast agent flow dynamics and the appearance of vessels in one or more projections at different points in time.

Starting from the arrangement shown in FIG. 2 and described in detail above, initial vessel segments of interest are again defined via a set of user-defined seed points (one or more). For downstream tracking of a vascular subsystem, first the local vessel direction and radius is extracted in all projection images $P_1, \ldots P_k, \ldots P_N$ (the results of this step are indicated in FIG. 4). Using a multi-scale approach, the probability that a pixel shows a projected vessel may be determined together with information on the local direction and radius of this vessel (cf. A. F. Frangi, W. J. Niessen, K. L. Vincken, M. A. Viergever: "Multiscale vessel enhancement filtering", Medical Inage Computing and Computer Assisted Interventions (MICCAI), Proc. LNCS 1496, pp. 130-137, 1998).

The iterative 3D vessel tracking illustrated in FIG. 5 uses a newly created Hough hypothesis space for direction and vessel radius and a mutual combination of the required continuity in vessel direction, vessel radius, and contrast agent filling. In image processing, a Hough hypothesis space is used to predict the location and orientation of an object which is known to be (anywhere) in a given volume. Different hypotheses (i.e. object parameters like location in x- and y-direction, size of the object, rotation angle of the object etc.) constitute the dimensions of a Hough space. The available image data or features are then separately tested to which object parameters they could belong, and these parameters are entered into the Hough space. Finally, the point in Hough space with the maximum of entries corresponds to the predicted hypotheses (cf. D. Ballard: "Generalized Hough transform to detect arbitrary patterns", IEEE Transactions on Pattern Analysis and Machine Intelligence, vol 13, no 2, pp 111-122, 1981).

For extraction of the local 3D direction in a currently considered, tracked point $\vec{x}$ on the vessel, the estimated TIC, i.e. the amount of contrast agent in a vessel at this point is also taken into account. During tracking, the TIC of the closest point upstream is a good estimation for the TIC at $\vec{x}$. The hypothesis space collects evidence for vessels in any 3D direction $\vec{o}$ and of any radius r based on above 2D vessel filter results obtained in the projections $P_1, \ldots P_k, \ldots P_N$ as shown in FIG. 4. The continuity of the contrast agent flow is included in this collection of evidence by weighting each entry reciprocal to the difference of attenuation at this point in space compared to the aforementioned estimation of the TIC, i.e. the contrast agent dynamics.

The Hough space for this search is initialized empty. Candidates for the next point in the vessel of interest are obtained when the last known cylinder element is elongated in direction of the last known orientation, which is varied up to a maximal bending angle. These candidate positions $\vec{x}_i$ are therefore placed on a spherical plane.

Then, for each projection $P_k$, the projected position $\vec{x}_i'$ of $\vec{x}_i$ in accordance to the imaging geometry $\vec{g}_k$ is determined. For each $P_k$, the vessel filter has been applied for one or more different vessel sizes σ, and a local vessel direction φ' and the strength of the vessel filter S have been determined. Here, S is interpreted as the probability that a vessel of size σ is contained in $P_k$ at position $\vec{x}_i'$, and φ' gives the planar orientation of this vessel. Depending on the imaging geometry $\vec{g}_k$, different orientations $\vec{o}$ can be present at $\vec{x}_i$ when the projected vessel orientation φ' is observed at $\vec{x}_i'$ and vessels of size σ are considered. For all possible $\vec{o}$, the hypothesis space is incremented by the filter strength $S_k$ extracted as feature in $P_k$. To include a-priori knowledge on the coherent flow of contrast agent through a vessel segment, the filter strength is weighted by a plausibility factor that compares the last known TIC in the extracted vessel segment with the TIC extracted at $\vec{x}_i$. The $S_k$ are individually weighted with the factor $$\frac{1}{1+|\Delta TIC_k|}$$

that decreases when the difference between observed and predicted contrast agent dynamics increases, therefore reducing the weighting of this less plausible hypothesis in the Hough space. This weighting can furthermore include the confidence measure of the TIC itself, which is described below.

The highest evidence in the hypothesis buffers determines the local radius $r_{opt}$ and direction $\vec{o}_{opt}$ of the tracked vessel segment, wherein the next point of the iteratively determined vessel geometry is determined by elongation of the vessel segment in direction $\vec{o}_{opt}$. With this estimation, then the local TIC at point $\vec{x}$ is extracted together with a confidence measure. To this end, the attenuation is read from the background-corrected input frames $P_1, \ldots P_k, \ldots P_N$ (using DSA or local background elimination). As the 3D direction of the vessel at $\vec{x}$ is now known, all attenuation values can be corrected for the virtual attenuation increase due to foreshortening in projections. The confidence of each TIC value is extracted based on the conformance of the 3D estimation and the projective estimation from the vessel filters. If the vessel segment of interest is occluded by other vascular structures or background attenuation, then this conformance and the respective confidence is low.

For noise reduction and to reduce the high degree of freedom, the confided measurements can be fitted to a parametric model function $c(t, \vec{p})$ of the TIC. An example of this model function is shown in FIG. 6. The fitting process optimizes the conformance of a measured TIC with a parameterized TIC by changing of few parameters.

In a further embodiment, a different model function $c(t, \vec{p})$ is used where a TIC is modeled by the simulation of the TIC at the point of injection (which is known if the start and stop of the contrast agent injection are observed) and the fluid transport of the mix of blood and contrast agent through a sequence of tubes where the length and radius of these tubes corresponds to the cylinder elements that build the geometric model.

When the tracking ends (e.g. at the border of the imaged volume or if no further stable hypothesizes are obtained), the 3D geometry of a vessel path and the local TICs along this path are known. Robust flow measurements can then be obtained that avoid the foreshortening and occlusion artifacts that are inherent to projective measurements.

As was already mentioned, FIG. 6 shows an exemplary course of a parametric model function (bold curve in the right diagram) for contrast agent dynamics or TICs of a point in a vessel in dependence on time. The contrast agent dynamics/TIC is in this example approximated by a linear spline with six parameters providing information about the inflow, a plateau with maximum contrast and outflow $(c(t; \vec{p}) \equiv c(t; t_{in}, t_{p1}, t_{p2}, t_{out}, c_{p1}, c_{p2}))$.

The proposed methods allow reconstructing the 3D vessel geometry and its visual appearance due to contrast flow from various acquisition protocols such as bi-plane or rotational acquisitions. They massively reduce the amount of acquired data that is otherwise required to reconstruct the respective amount of diagnostically relevant information. In particular, the approaches and respective acquisition protocols can be realized on C-arm based X-ray systems with their specifics regarding detector frame rate and rotational speed. Furthermore, the method can improve overall robustness and stability of 3D geometry reconstruction as they can account for the dynamic appearance due to flow. The proposed extraction of the vascular geometry and flow dynamics may for example be applied in neurovascular diagnostics, but is applicable to peripheral or central vascular systems as well. The methods can be added to existing 3D vessel reconstruction software packages.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. Investigation system for the determination of vessel geometry and flow characteristics in a vessel system, comprising:
    an X-ray device for generating differently oriented projections of a vessel system during a passage of a bolus of contrast agent therethrough, the projections including data representative of contrast agent dynamics within the vessel system;
    a data processing unit adapted to receive data representative of at least some of the differently oriented projections from the X-ray device and adapted to reconstruct a three-dimensional model of a geometry and flow characteristics of the vessel system from received data generated in a single temporal sequence with the use of predetermined modeled contrast agent dynamics.

2. The system according to claim 1, wherein the data processing unit comprises a parametric model of both the vessel geometry and the contrast agent dynamics.

3. The system according to claim 2, wherein the data processing unit is adapted to reconstruct an instance of the model that fits both to the sequence of X-ray projections $(P_1, P_k, P_N)$ and to plausibility rules for vessel geometry and contrast agent dynamics.

4. The system according to claim 2, wherein the parametric model comprises elements corresponding to local vessel segments and local contrast agent dynamics, wherein each of said elements is associated with a local plausibility score value.

5. The system according to claim 4, wherein the data processing unit is adapted to reconstruct an instance of the model by determination of an optimal path with respect to the local plausibility score values.

6. The system according to claim 3, wherein the data processing unit is adapted to reconstruct the flow characteristics and the vessel geometry in three dimensions progressively along the vessels.

7. The system according to claim 1, wherein the data processing unit is adapted to predict a function $(c(t, \vec{p}))$, wherein c represents an amount of contrast agent at time t at a point $\vec{p}$, the function c yielding a time-intensity curve of the vessel structure.

8. The system according to claim 1, further comprising an input device, and wherein the data processing unit is adapted to start the reconstruction of the vessel geometry from user-defined seed points.

9. The system according to claim 1, further comprising a display unit for displaying the reconstructed vessel geometry and/or the reconstructed flow characteristics.

10. A method for the determination of the vessel geometry and the flow characteristics in a vessel system, comprising:
    a) injecting a bolus of contrast agent into a vessel system;
    b) generating a temporal sequence of X-ray projections $(P_1, P_k, P_N)$ of the vessel system during a passage of said bolus from different directions;
    c) reconstructing a three-dimensional vessel geometry and flow characteristics of at least a portion of the vessel system with the use of projections generated in a single temporal sequence and predetermined model contrast agent dynamics.

11. The method recited in claim 10, wherein the reconstructing comprises:
    extracting at least one set of image features from the received data;
    using an optimization algorithm, comparing a predetermined geometric and flow-dynamic model of a vascular subsystem with the extracted image features; and
    determining from the comparison a best fit therebetween, the best fit comprising the reconstructed three-dimensional model.

12. The method recited in claim 11, wherein the image features comprise a position, a local orientation, and a local diameter of dark, elongated structures in the received data, and the extracting comprises using an eigenvalue analysis of a Hessian matrix extracted at a plurality of scales.

13. The method recited in claim 11, wherein the image features comprise at least one of a time of bolus arrival, a length of the bolus, and a dispersion of a front of the bolus, and the extracting comprises fitting the image features to a time-intensity curve at a plurality of positions calculated from the received data.

14. The method recited in claim 13, wherein the optimization algorithm using and determining comprise:
    dividing the vessel system into a plurality of tubular vessel segments;

fitting parameters extracted from the image features with the predetermined model for each tubular vessel segment;

calculating a plausibility score for the predetermined model, the image features, and the time-intensity curve;

inserting the plausibility score into a three-dimensional map;

calculating a minimal cost path through the three-dimensional map; and reconstructing a section of the vessel system from the minimal cost path.

15. The method recited in claim 14, wherein the minimal-cost-path calculating comprises using a front propagation algorithm.

16. The method recited in claim 13, wherein the optimization algorithm using and determining comprise using an iterative tracking algorithm adapted to add successive tubular segments, starting from a defined point, a direction of the adding determined from a calculated highest plausibility score.

17. The method recited in claim 16, wherein the plausibility score is calculated as a weighted combination of a consistency of a hypothetical direction of a next tubular segment in three dimensions as compared with all planar directions extracted as image features.

18. The method recited in claim 16, wherein the plausibility score is calculated from the time-intensity curve of a preceding tubular segment in comparison with a time-intensity curve extracted for a next tubular segment in a hypothetical direction.

19. A record carrier on which a computer program for the determination of the vessel geometry and the flow characteristics in a vessel system is stored, said program being adapted to execute a method according to claim 10.

20. A system for determining vessel geometry and flow characteristics in a vessel system, comprising:

an input for receiving X-ray image data representative of a single temporal sequence of differently oriented projections of a vessel system during a passage of a bolus of contrast agent therethrough, the projections including data representative of contrast agent dynamics within the vessel system;

a data processing unit adapted to reconstruct a three-dimensional model of a geometry and flow characteristics of the vessel system from the received data with the use of predetermined modeled contrast agent dynamics; and an output for outputting the reconstructed three-dimensional model.

21. The system recited in claim 20, wherein the data processing unit comprises a plurality of modules comprising:

a first module comprising an algorithm for extracting at least one set of image features from the received data;

a second module comprising a predetermined geometric and flow-dynamic model of a vascular subsystem; and a third module comprising an optimization algorithm for comparing the predetermined model of the second module with the extracted image features from the first module and determining from the comparison a best fit therebetween, the best fit comprising the reconstructed three-dimensional model.

22. The system recited in claim 21, wherein the image features comprise a position, a local orientation, and a local diameter of dark, elongated structures in the received data, and the first module algorithm comprises an eigenvalue analysis of a Hessian matrix extracted at a plurality of scales.

23. The system recited in claim 21, wherein the image features comprise at least one of a time of bolus arrival, a length of the bolus, and a dispersion of a front of the bolus, and the first module algorithm comprises fitting the image features to a time-intensity curve at a plurality of positions calculated from the received data.

24. The system recited in claim 23, wherein the third module comprises code segments adapted to:

divide the vessel system into a plurality of tubular vessel segments;

fit parameters extracted from the image features with the predetermined model of the second module for each tubular vessel segment;

calculate a plausibility score for the predetermined model, the image features, and the time-intensity curve;

insert the plausibility score into a three-dimensional map;

calculate a minimal cost path through the three-dimensional map; and reconstruct a section of the vessel system from the minimal cost path.

25. The system recited in claim 24, wherein the minimal-cost-path calculation comprises using a front propagation algorithm.

26. The system recited in claim 23, wherein the third module comprises an iterative tracking algorithm adapted to add successive tubular segments, starting from a defined point, a direction of the adding determined from a calculated highest plausibility score.

27. The system recited in claim 26, wherein the plausibility score is calculated as a weighted combination of a consistency of a hypothetical direction of a next tubular segment in three dimensions as compared with all planar directions extracted as image features.

28. The system recited in claim 26, wherein the plausibility score is computed from the time-intensity curve of a preceding tubular segment in comparison with a time-intensity curve extracted for a next tubular segment in a hypothetical direction.

* * * * *